United States Patent [19]

Strickland

[11] Patent Number: 5,507,800
[45] Date of Patent: Apr. 16, 1996

[54] CARPAL TUNNEL TOME AND CARPAL TUNNEL RELEASE SURGERY

[76] Inventor: James W. Strickland, 7979 S. 100 East, Zionsville, Ind. 46077

[21] Appl. No.: 242,366

[22] Filed: May 13, 1994

Related U.S. Application Data

[63] Continuation-in-part of Ser. No. 61,855, May 14, 1993, Pat. No. 5,387,222.

[51] Int. Cl.$^6$ .................................................. A61B 17/32
[52] U.S. Cl. .............................................. 606/167; 30/294
[58] Field of Search ............................ 606/167, 166, 606/170; 128/898; 30/289, 294

[56] References Cited

U.S. PATENT DOCUMENTS

| | | |
|---|---|---|
| 3,365,798 | 1/1968 | Cunningham . |
| 3,831,274 | 8/1974 | Horrocks . |
| 3,975,822 | 8/1974 | Mabus . |
| 4,026,295 | 5/1977 | Lieberman . |
| 4,962,770 | 10/1990 | Agee et al. . |
| 5,029,573 | 7/1991 | Chow . |
| 5,273,024 | 12/1993 | Menon et al. . |

FOREIGN PATENT DOCUMENTS 2203341  10/1988  United Kingdom ................... 606/167

OTHER PUBLICATIONS

David M. Pagnanelli, M.D. et al., "Bilateral Carpal Tunnel Release at One Operation: Report of 228 Patients," *Neurosurgery*, vol. 31, No. 6, Dec. 1992.
David M. Pagnanelli, M.D. et al., "Carpal tunnel syndrome: surgical treatment using the Paine retinaculatome," *J. Neurosurg.*, vol. 75, Jul. 1991.
Kenneth W. E. Paine, M.D. et al., "Decompression using the Paine retinaculotome," *J. Neurosurg.*, vol. 59, Dec. 1983.
Ruggles Corporation Catalog, R-520 PAINE's Carpel Tunnel Retinaculotome, p. 59.

*Primary Examiner*—Stephen C. Pellegrino
*Assistant Examiner*—William W. Lewis
*Attorney, Agent, or Firm*—Woodard, Emhardt, Naughton, Moriarty & McNett

[57] ABSTRACT

An improved carpal tunnel tome for performing carpal tunnel release surgery is provided. In a first embodiment, a carpal tunnel tome including a slender handle with a blade at one end is provided. The blade is bounded on both sides by a pair of relatively blunt protuberances that extend distally beyond the cutting edge of the blade. In another embodiment, a carpal tunnel tome having a stem is provided. A cutting head, including a blade, is connected to the stem. One portion of the stem is angled so as to facilitate the use of the device in a small wound. The blade is bounded on one side by a short beveled protuberance, and on the other side by a longer blunted protuberance. In one embodiment, a disposable carpal tunnel tome is provided. The surgical procedure utilizing the tome requires only a single small incision in the palm of the patient's hand adjacent the distal end of the transverse carpal ligament. The instrument is then placed in the incision straddling the ligament and is then advanced proximately toward the patient's wrist until the transverse carpal ligament is completely divided. The instrument is then withdrawn and the incision is closed with one or two sutures and an appropriate dressing is applied.

34 Claims, 14 Drawing Sheets

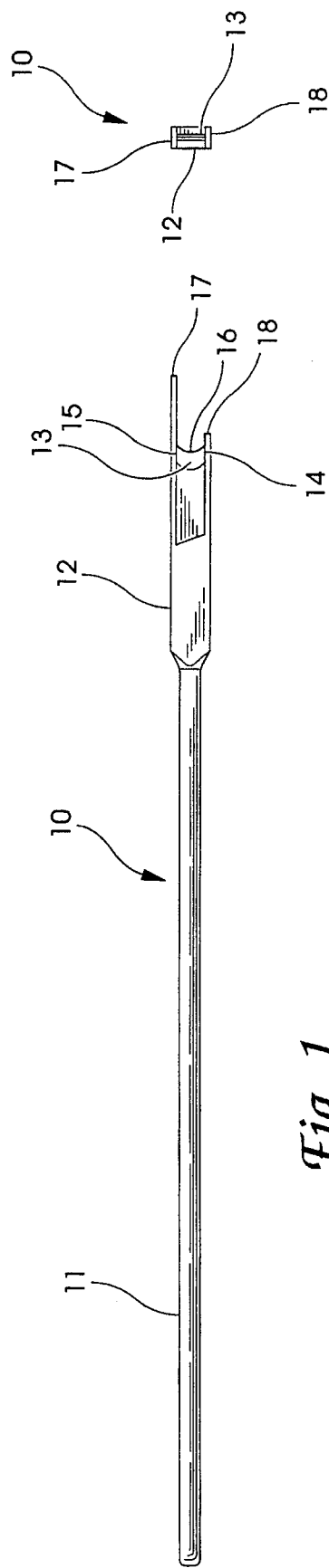
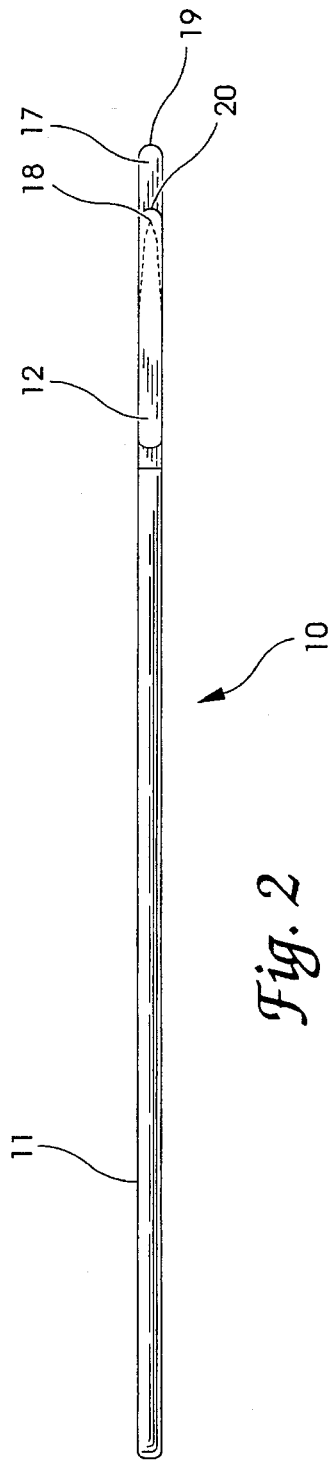
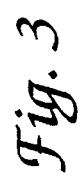

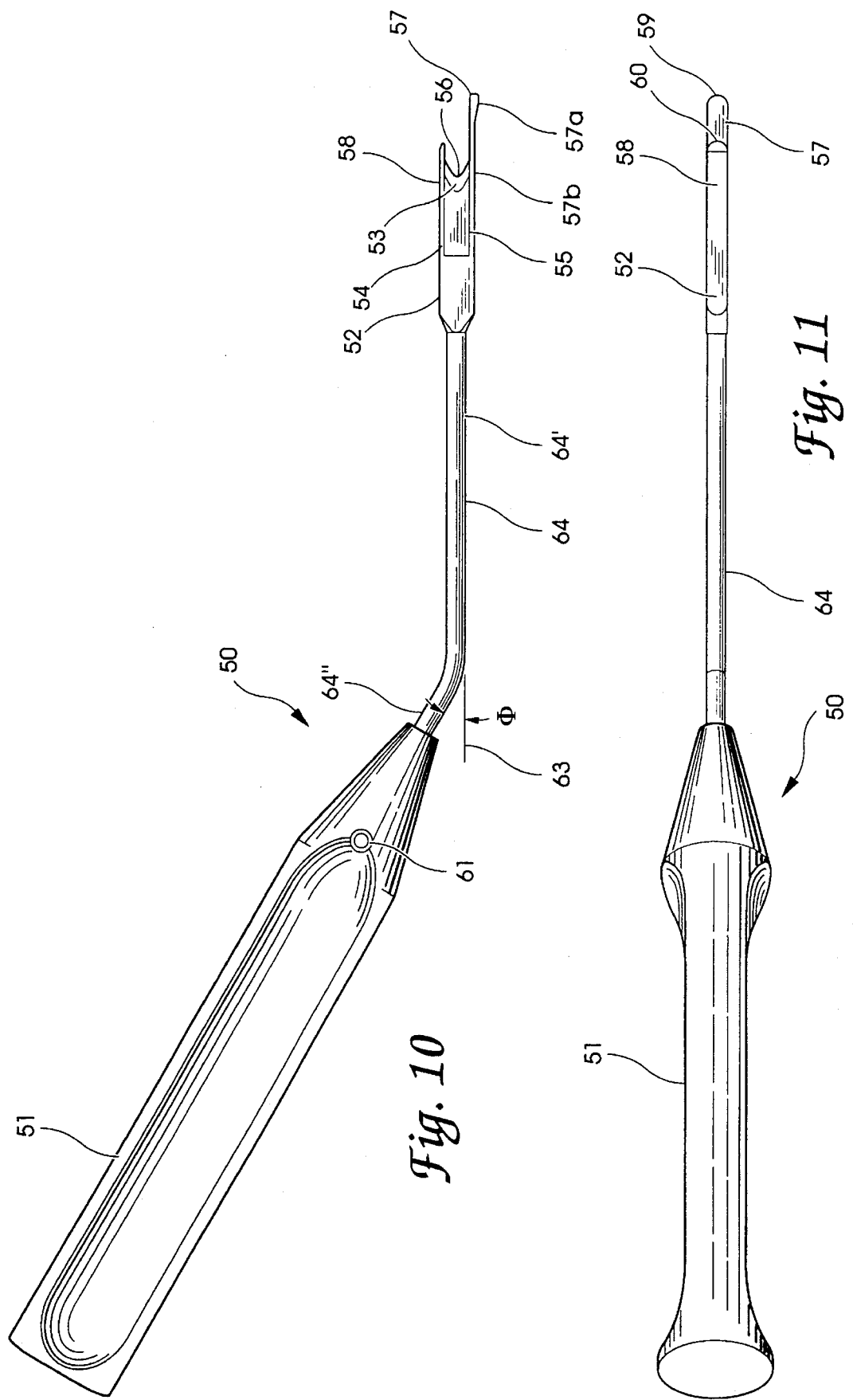

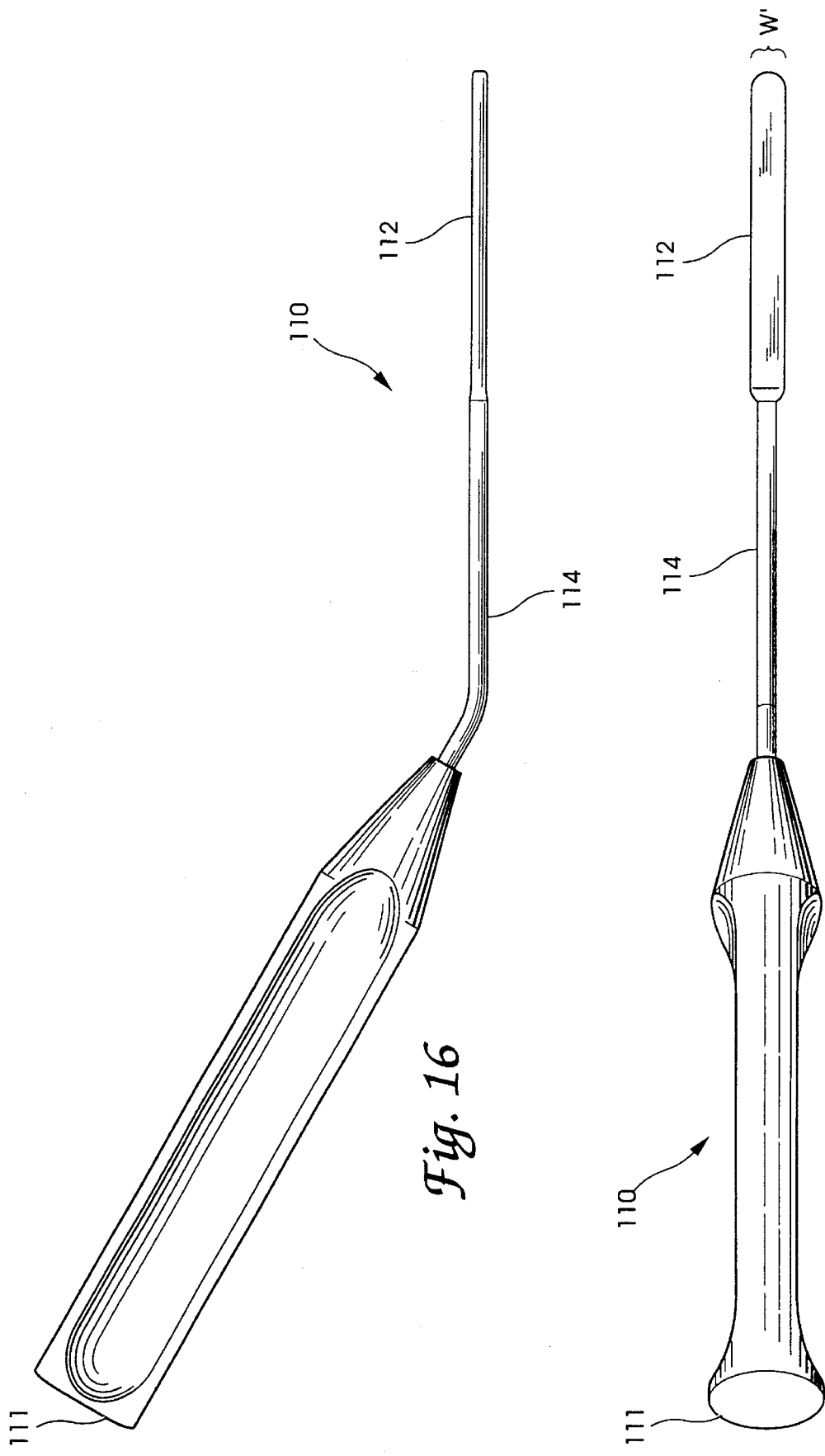

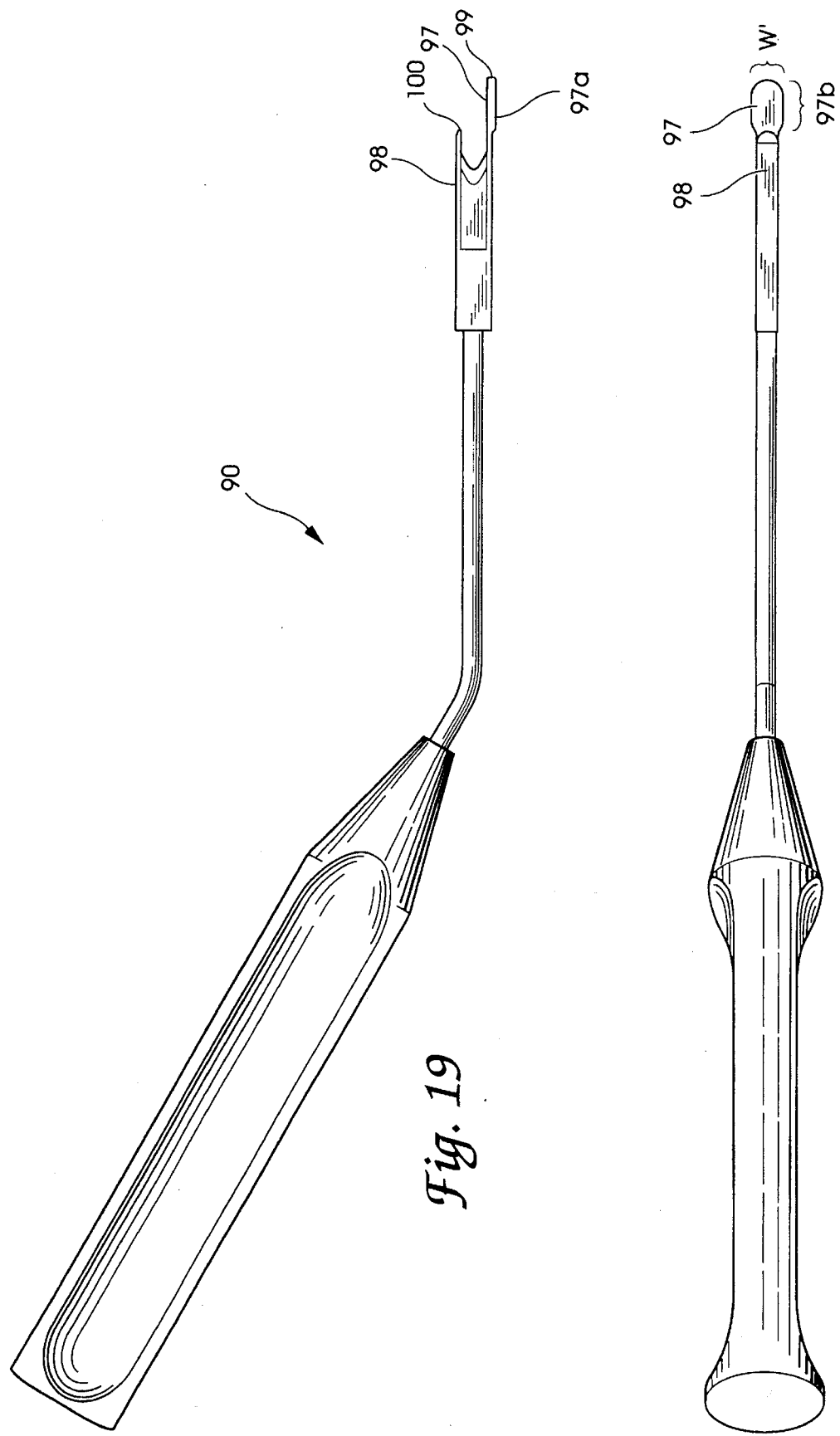

CARPAL TUNNEL TOME AND CARPAL TUNNEL RELEASE SURGERY

REFERENCE TO RELATED APPLICATIONS

This application is a continuation-in-part of U.S. patent application Ser. No. 08/061,855, filed on May 14, 1993 now U.S. Pat. No. 5,387,722 by the same inventive entity, and entitled CARPAL TUNNEL TOME AND CARPAL TUNNEL RELEASE SURGERY.

BACKGROUND OF THE INVENTION

The present invention relates generally to surgery, and in particular to the use of a carpal tunnel tome to perform carpal tunnel release surgery.

Surgical decompression of the carpal tunnel, which is often referred to as carpal tunnel release surgery, is the most commonly performed surgical procedure in the United States. The condition is frequent in middle-aged persons whose job requires exposure to vibrating tools or chronic, repetitious use of the hands, such as on keyboards or on assembly lines. Carpel tunnel syndrome is normally characterized by some combination of wrist pain, forearm aching, and/or pain, tingling and numbness in the thumb, index and middle fingers. The pain results from compression of the median nerve in an anatomic passageway in the wrist and palm that is frequently referred to as the carpal tunnel.

Historically, the operative procedure designed to eliminate the symptons of carpal tunnel syndrome includes making an incision in the palm—sometimes extending across the wrist—to divide the deep transverse carpel ligament and its proximal fascial extension, and release the pressure on the median nerve. Although the procedure has been highly successful in relieving most patients' symptons, it is often complicated by tenderness around the incision site in the proximal palm and across the wrist. In addition, patients frequently experience "pillar pain" at the base of the thenar and hypothenar eminences, just distal to the wrist crease and on each side of the surgical scar. This post-surgical discomfort has been implicated as the cause for the slow return of patients to occupational activities following conventional carpal tunnel release surgery.

In recent years, there have been efforts made to alter the technique of carpal tunnel release surgery in an effort to minimize the amount of proximal palm and pillar pain, and allow patients to resume normal occupational and domestic activities more quickly. One such method involves making a relatively shorter incision located entirely in the palm and then dividing the deep transverse carpal ligament by straddling the ligament with small blunt scissors which are passed proximately toward the patient's wrist. Although this technique is effective, there is some danger of inadvertent injury to the median nerve or other structures from the tip of the scissors as they are blindly passed in a proximal direction. Further, the length of incision required in order to divide the majority of the ligament prior to scissor passage, may still be large enough to lead to some palmar pain.

The use of one of several endoscopic methods for division of the deep transverse carpal ligament has also received considerable popularity during the past several years. These techniques employ the passage of a special instrument beneath the carpal ligament, such as for example, the method shown in U.S. Pat. No. 5,029,573 to Chow, and then utilize fiberoptics and special cutting instruments to observe and divide the ligament. Although efforts have been made to make these techniques as simple and safe as possible, they still require specialized training and a reasonably long learning curve before the surgeon becomes adept at their use. Complications such as injury to or division of, the median nerve, one of its branches, the tendons within the carpal vault or the superficial arterial arch of the palm have been described with disconcerting frequency. In some reported cases, the instrument has actually been passed into the wrong passageway where injury may occur to the ulnar nerve or artery. Endoscopic carpal tunnel release surgery averages from 30 to 60 minutes for completion and can be done under either a general or local anesthesia. Apart from being a rather lengthy procedure, endoscopic techniques have been challenged as not always being consistent in their ability to completely divide the transverse carpal ligament.

What is needed is a simple, safe and effective technique for division of the deep transverse carpal ligament that requires only a small mid-palmar incision and utilizes a small cutting instrument designed to protect adjacent tissues when cutting the ligament.

SUMMARY OF THE INVENTION

The present invention is directed to a carpal tunnel tome, one embodiment of which comprises a handle and a blade which is attached to a cutting head at the distal end of the carpal tunnel tome. The blade has a cutting edge pointing distally away from the distal end of the handle and is concealed between a pair of protuberances that are attached on either side of the blade and extend distally beyond the cutting edge. The first protuberance of the pair extends distally away from the cutting edge a significantly larger distance than the second protuberance. In a first embodiment, the handle is a slender elongate handle which extends up to and connects with the proximal end of the cutting head. In a second embodiment, the handle and cutting head are connected via a stem. The handle may be removable from the stem or integrally formed with the stem. Additionally, the stem may optionally be angled. Further, the unit may be manufactured as either a completely reusable tool, as a partially disposable tool or as a completely disposable unit.

One object of the present invention is to provide an improved instrument and method for performing carpal tunnel release surgery.

Another object of the present invention is to provide a surgical method that results in less trauma to the patient and quicker post-operative recovery.

Related objects and advantages of the present invention will be apparent from the following description.

BRIEF DESCRIPTION OF THE DRAWINGS

FIGS. 1–3 are side, bottom and end views, respectively of an orthographic projection of a carpal tunnel tome according to one embodiment of the present invention.

FIGS. 10–12 are side, bottom and end views, respectively of an orthographic projection of a carpal tunnel tome according to a second embodiment of the present invention.

FIGS. 16–18 are side, bottom and end views, respectively of an orthographic projection of a probe for use in connection with the carpal tunnel surgery described herein.

FIGS. 19–21 are side, bottom and end views, respectively of an orthographic projection of a carpal tunnel tome according to an additional embodiment of the present invention.

DESCRIPTION OF THE PREFERRED EMBODIMENT

Figure 4:
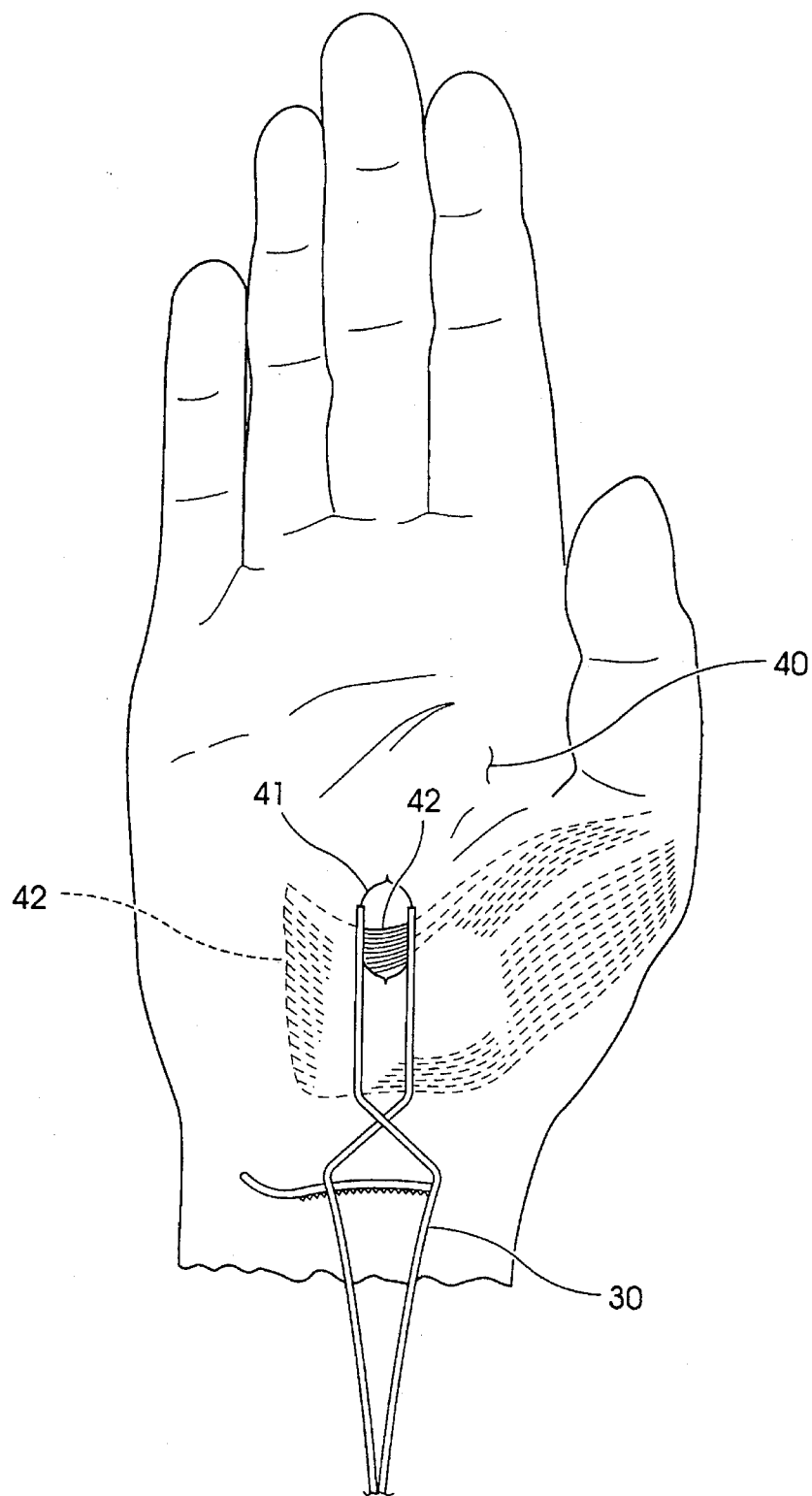
FIGS. 4–6 and 8–9 are views of the palmar side of a patient's hand and wrist showing serially the carpal tunnel release surgery according to the technique of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIGS. 1–3, a carpal tunnel tome 10 according to a first embodiment of the present invention includes a slender cylindrical handle 11 having a head portion 12 integrally formed thereon. If desired or deemed necessary, handle 11 and head portion 12 could be formed separately and attached to one another by one of several means known in the art. The head portion includes a blade 13 having a cutting edge 16 which is bounded on one side 15 by a relatively blunt protuberance 17 and on its other side 14 by another but shorter blunt protuberance 18. Cutting edge 16 is preferably concave as shown but could also hake on other shapes, such as, for example, a slant or V-shape. Both blunt protuberances 17 and 18 project distally beyond cutting edge 16 so that blade 13 is concealed within a channel defined by the blunt protuberances. Head portion 12 is made to have a sufficient width that both blunt protuberances 17 and 18 are provided with rounded distal ends 19 and 20, respectively. In one preferred embodiment, blunt protuberance 17 extends roughly 7 mm distally beyond the other blunt protuberance 18. The reason for this preference will become better understood in reference to the surgical technique utilizing tome 10 described infra.

Another key feature of tome 10 is that blade 13 preferably has a width on the order of about 3 mm, which corresponds roughly to the thickness of the transverse carpal ligament in most adults. Finally, blunt protuberances 17 and 18 are preferably relatively flat surfaces oriented parallel to one another, with each having sufficient thickness to avoid the danger of accidental cutting or damage to tissue contacted by the blunt protuberances. In the preferred embodiment, blunt protuberances 17 and 18 have a thickness on the order of about 1 mm.

As can be seen from FIGS. 1–3, the head 12 and the portion of the handle 11 contiguous to the head 12 have dimensions in height and width which are no greater than the dimensions in cross section of the blade 16 and protuberances 17 and 18.

Figure 12:
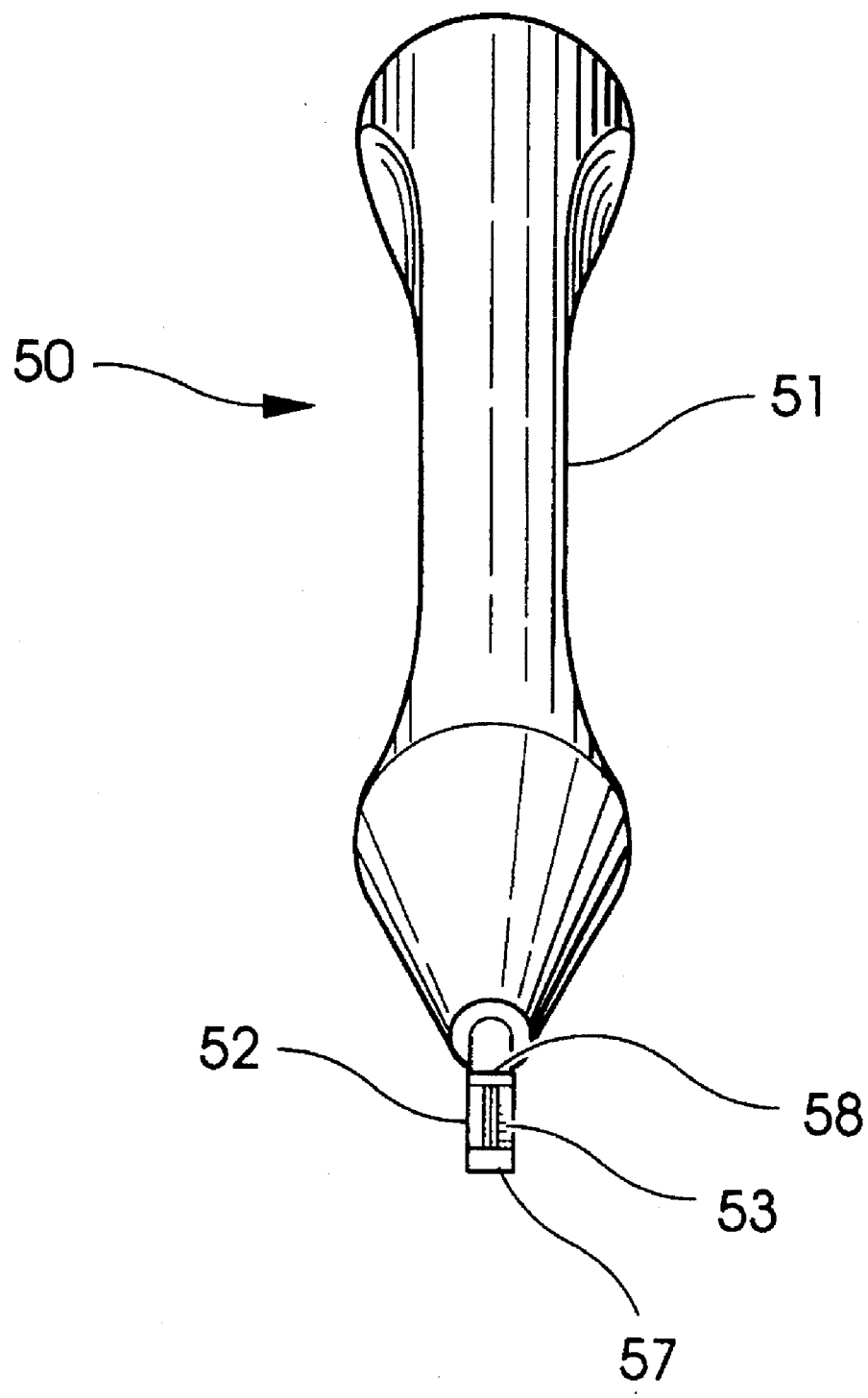

Referring now to FIGS. 10–12, there is shown a carpal tunnel tome 50 in accordance with a second embodiment of the present invention. Carpal tunnel home 50 includes a removable handle 51 attached, via set screw 61, to a stem 64, having a head portion or cutting head 52 integrally formed thereon. The head portion 52 is sharply beveled where it attaches to stem 64 so as to prevent the cutting head from catching on tissue when the instrument is withdrawn. The stem 64 includes a main body portion 64' and an angled portion 64". The main body portion 64' lies parallel to an axis 63. The angled portion 64" of the stem 64 is angled φ° from the axis 63. In one preferred embodiment, the angle φ is preferably 30°. The purpose of angling stem 64 is to facilitate the approach and entry into the small wound used to identify and divide the transverse carpal ligament.

If desired, handle 51, stem 64 and cutting head 52 could be formed integrally by several means known in the art. Further, in the present embodiment handle 51 has been streamlined and contoured to provide a better fit for the surgeons hand and, particularly, to improve the purchase of the index finger and thumb as the instrument is gently pushed to divide the ligament. For example, handle 51 includes two longitudinal channels formed into the handle and separated by the body of the handle, so as to provide for better gripping of the handle 51. Additionally, the handle could be contoured in other ways, for example having individual vertical finger grooves, or a roughened improved grip surface.

The head portion 52 of the carpal tunnel tome 50 includes a blade 53 having a cutting edge 56 which is bounded on one side 55 by a relatively blunt protuberance 57 and on its other side 54 by a shorter, tapered or beveled, blunt protuberance 58. The protuberance 58 is tapered so that the thickness of the protuberance is smoothly and continuously decreased over the last millimeter or so before the tip 60 of the protuberance 58. The set screw 61 may be used to secure the proximal end of the angled portion 64" of the stem 64 to the handle in such a manner as to allow the removal and change of cutting heads in case the cutting edge 56 of the instrument 50 becomes dull, in which case the stem 64 and cutting head 52 may be discarded while the handle 51 is retained. Alternatively, the set screw may be omitted and the handle may be molded integrally with the stem.

The shorter protuberance 58 of cutting head 52 has been tapered to better allow it to pass through the tough fibers that join the palmar fascia to the transverse carpal ligament. The bevel of protuberance 58 has been designed to minimize the possibility for penetration through the subcutaneous tissues and skin of the wrist at the completion of the division of the ligament.

Additionally, blunt protuberance 57 of the cutting head 52 has been provided with a thickened, blunted tip portion 57a to allow the protuberance 57 to pass smoothly along the under-surface of the ligament and to assure that there can be no injury to the underlying tendons or to the median nerve during transit. The distal ends of the protuberances 57 and 58 are rounded. However, the distal end of the protruberance 58 may, alternatively, be slightly more pointed, so as to allow it ho pass through the tough fibers more easily. The blunted tip 57a provides a margin of safety in case the instrument 50 were to be used in such a manner that the longer protuberance 57 would actually dive into the carpal tunnel and make contact with the underlying structures, such as the median nerve and the flexor tendon. Further, the thickened blunted tip 57a prevents the inadvertent passage down the wrong tissue plane in the proximal palm. The dense tissues above the carpal ligament could not be penetrated easily by this blunted tip 57a and the difficulty with its passage would immediately signal the surgeon that the lower protuberance 57 was not beneath the partially divided transverse carpal ligament, but had strayed above the ligament. Protruberance 57 and 58 are generally parallel to each other.

Cutting edge 56 is shown as being U-shaped, or nearly V-shaped, but could also take on other shapes, such as for example, a slant or concave, as with the embodiment of FIGS. 1–3. Both protuberances 57 and 58 project distally beyond cutting edge 56 so that blade 53 is concealed within a channel defined by the protuberances. Head portion 52 is made to have a sufficient width such that protuberances 57 and 58 are provided with rounded tips 59 and 60, respectively.

In the preferred embodiment, blunt protuberance 57 extends roughly 7 mm distally beyond the other blunt protuberance 58 and the distal ends 59 and 60 of both protuberances extend beyond the cutting edge 56. The reason for this preference will become better understood in reference to the surgical technique utilizing tome 50 described infra. Note that the use of carpal tunnel tome 50 during an operative procedure is identical to the use of the embodiment shown in FIGS. 1–3.

As with the embodiment of FIGS. 1–3, tome 50 has a blade 53 preferably having a width on the order of about 3 mm, which corresponds roughly to the thickness of the transverse carpal ligament in most adults. Finally, the surfaces of protuberances 57 and 58 which bound the blade and extend distally therefrom are preferably relatively flat surfaces oriented parallel to one another. In the preferred embodiment of tome 50, the thickness of the blunt protuberance 57, measured at its distal tip 57a, is about 2 mm, tapering away from the distal tip to the reduced portion 57b having a thickness of about 1 mm. The width of beveled protuberance 58 distal from its beveled tip and the width of the blunt protuberance 57 are equal.

The head 52 and the portion of the stem 64 contiguous to the head 52 have dimensions in height and width which are no greater than the dimensions in cross section of the blade 56 and protuberances 57 and 58.

Figure 15:
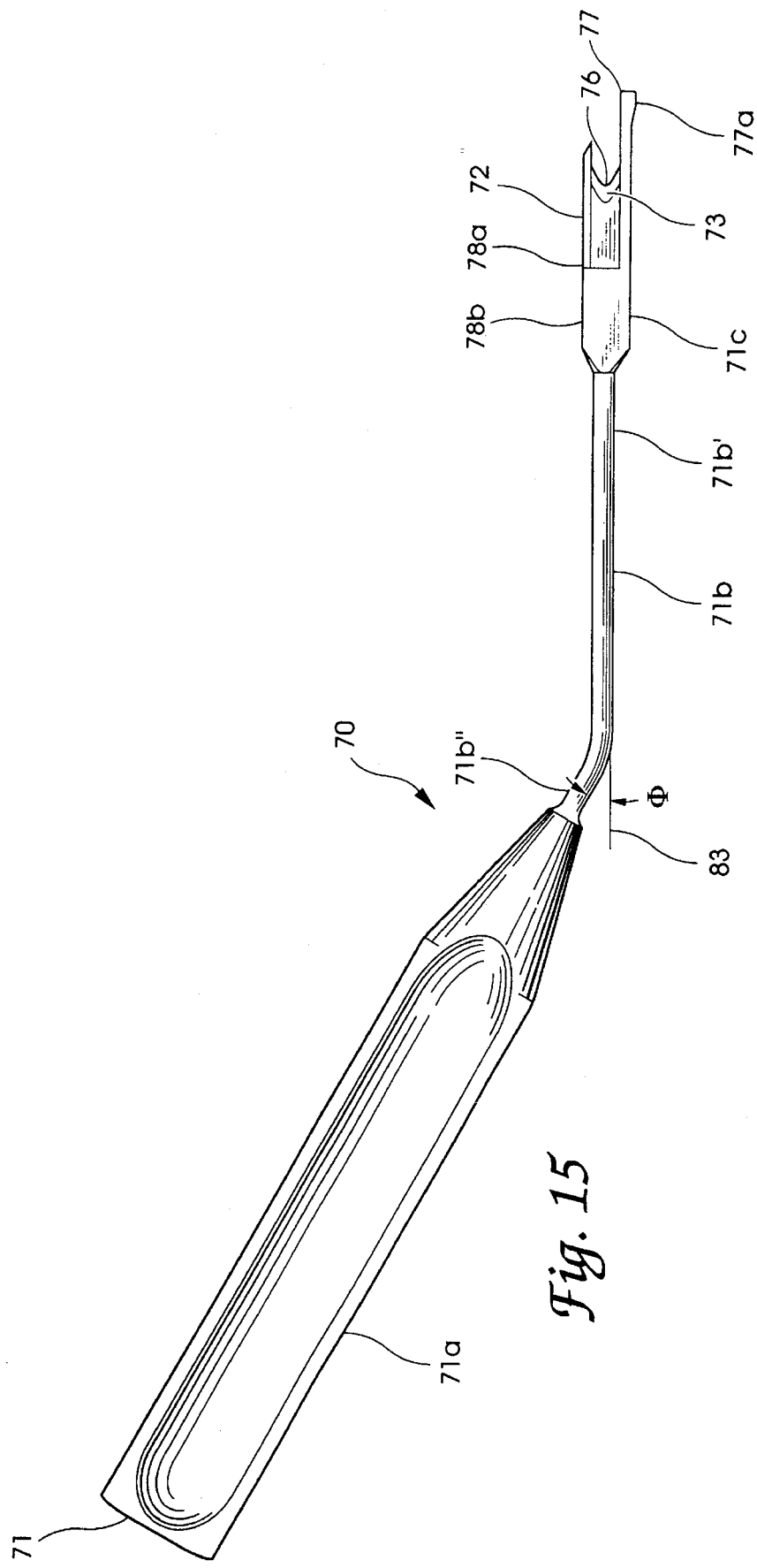
FIG. 15 is a side planar view of a carpal tunnel tome in accordance with a third embodiment of the present invention.

Referring now to FIG. 15, there is shown another embodiment of the carpal tunnel tome of the present invention wherein the carpal tunnel tome 70 is designed as a disposable unit. In many respects the carpal tunnel tome 70 is similar to the carpal tunnel tome 50 of FIGS. 10–12. As such, the method of using the carpal tunnel tome 70 is identical to that of the devices shown in FIGS. 1–3 and FIGS. 10–12 and additionally described herebelow. However, the carpal tunnel tome 70 of FIG. 15 has been designed as a two piece construction wherein the handle 71a, the stem 71b and a portion of the cutting head 71c, including the lower protuberance 77, are all integrally formed as a first portion 71 of the instrument 70. The first portion 71 may be integrally made of a single material, such as plastic, but may additionally be made from a metal such as stainless steel.

The second portion 72 of the instrument 70 includes the beveled or sharpened protuberance 78 and the blade 73, including edge 76, and is preferably made from stainless steel. The second portion 72 is fixed and mounted to the cutting head 71c of first portion 71, in any known manner such as injection molding, so as to securely mount the portion 72 on the cutting head. The integrally formed lower protuberance 77 is widened and blunted at its tip 77a, as in the embodiment of FIGS. 10–12, and is likewise, longer than the protuberance 78. Likewise, the shorter protuberance 78 is beveled to facilitate passage of the instrument 70. An angled portion 71b'' of the stem 71b, proximal to the handle 71a is angled $\phi°$ from an axis 83 parallel to the longitudinal axis of the main portion 71b' of the stem 71b. Again the handle 71a is contoured to allow the surgeon to better grip the instrument during use. The instrument of FIG. 15 is the same as that shown in FIGS. 10–12 in all other respects, with the exception being that since the handle 71a and stem 71b are integrally formed, a set screw is not necessary to couple the two members.

Figure 21:
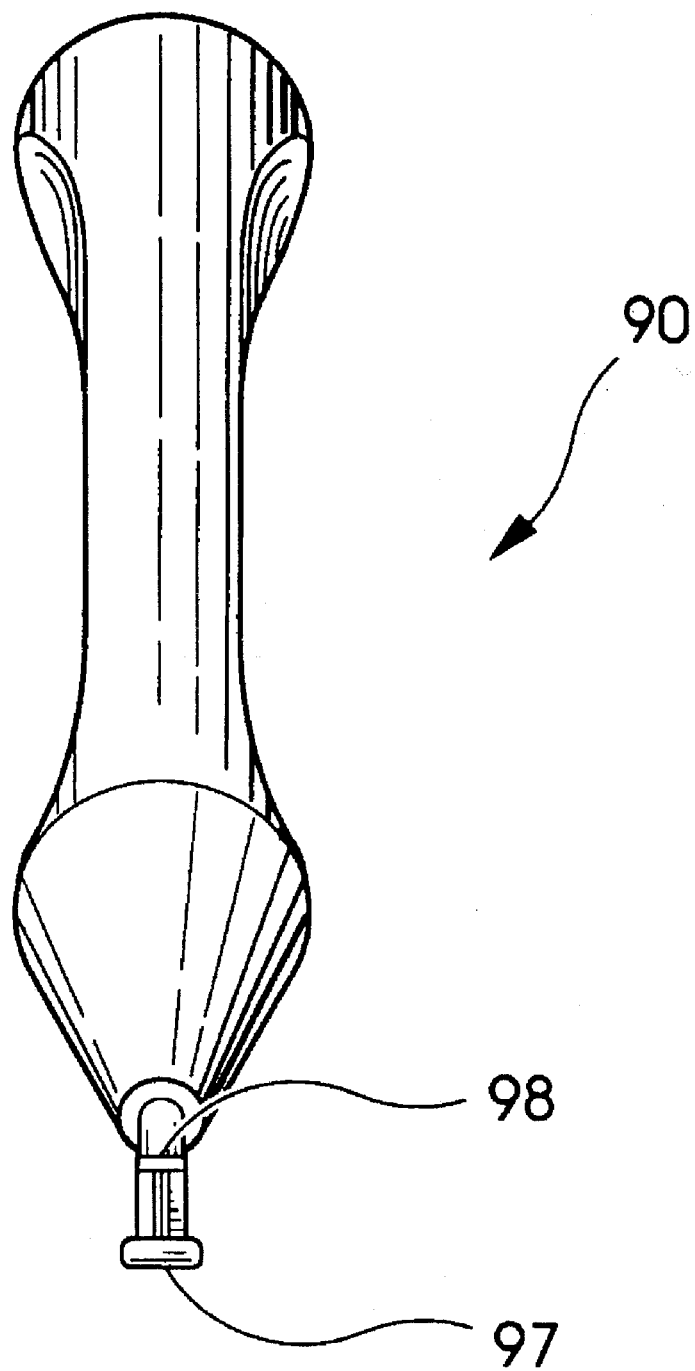

Referring now to FIGS. 19–21, there is shown a further embodiment of the carpal tunnel tome of the present invention. The carpal tunnel tome 90 is virtually identical to that of FIGS. 10–12 with two exceptions. First, in FIG. 19 the handle 91 of the carpal tunnel tome 90 is shown as being integrally formed to the stem, thus the set screw 61 of FIG. 10 has been omitted. Second, the distal hip 99 of the lower protuberance 97 has been widened, as well as thickened, so as to allow that portion of the carpal tunnel tome to clear the area in advance of the passage of the remainder of the cutting head. Additionally, the use of a wider protruberance on the cutting head has the advantage of providing even further protection against damaging the median nerve and flexor tendon, by preventing the inadvertent passage of the cutting head down the wrong tissue plane in the proximal palm. As can be seen in from FIGS. 19 and 20, the widened portion 97b of the protuberance 97 extends beyond the tip 100 of the shorter protuberance 98.

Figure 13:
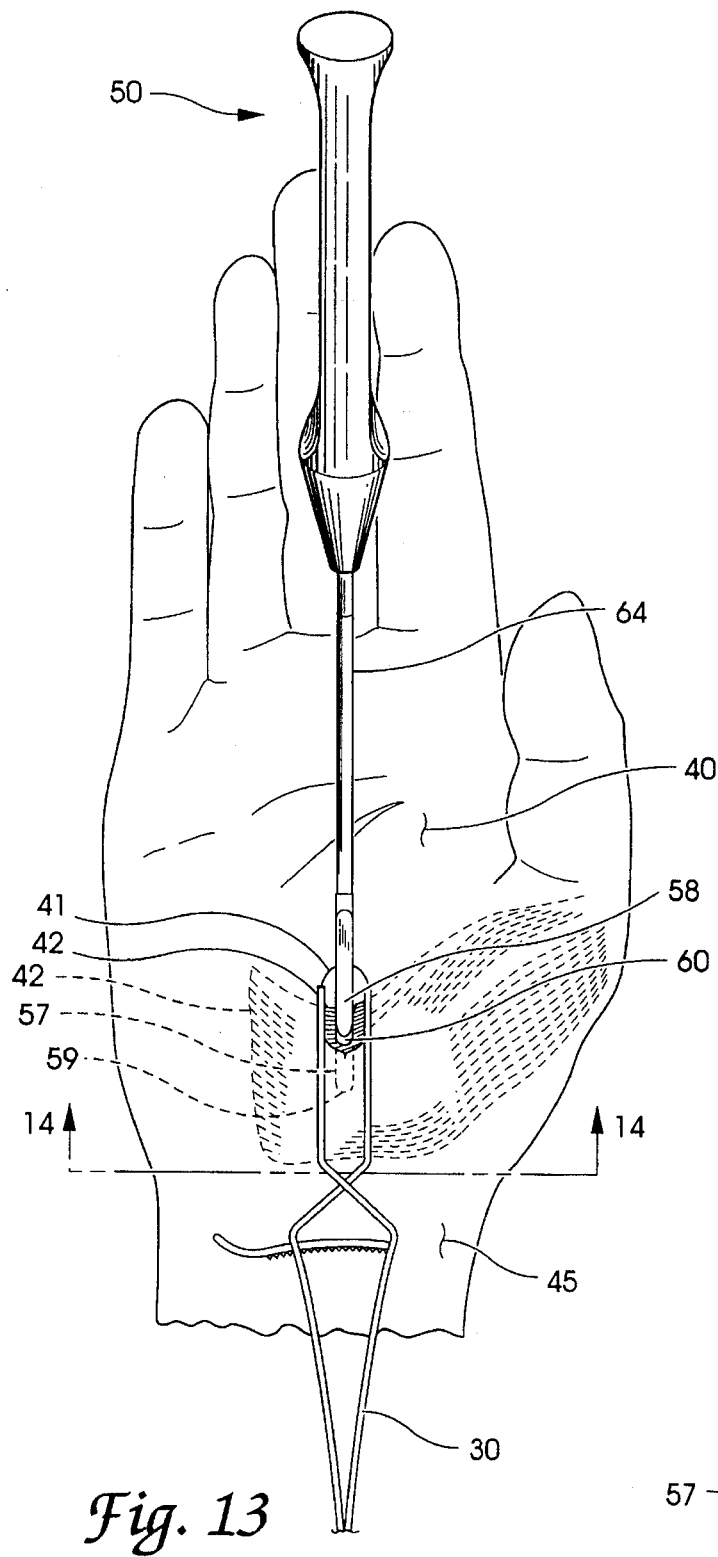
FIG. 13 is a view of the palmar side of a patient's hand and wrist showing the use of the carpal tunnel tome of FIGS. 10–12 and FIG. 15 in the carpal tunnel release surgery according to the technique of the present invention.
Figure 14:
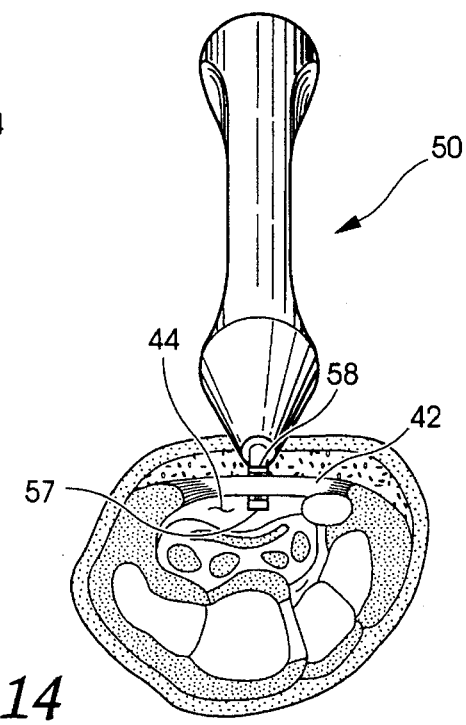
FIG. 14 is a cross-section through the patient's wrist at a midpoint in the surgery looking in the direction of arrows 14—14 of FIG. 13.

In one example of the present embodiment, the widened portion of the distal tip 99 of the protruberance 97 has a width w of about 5 millimeters. That width is about 1.5 millimeters greater than the widths of the protruberance 98 and of the proximal portion of the protruberance 97 at the cutting head, which are both about 3.5 millimeters wide. Additionally, the widened portion 97b begins at the point where the upper protruberance 98 ends. Further, in the device of the present example, the greatest thickness at the distal tip 99 of the protruberance 97 is about 2.75 millimeter, in contrast to a 2.0 millimeters thickness proximal to the cutting blade. Further, in this particular example, the entire widened portion 97b of the lower protruberance 97 extends beyond the end of the protruberance 98 a length of about 8 millimeters. As such, it should be understood from the above description that the carpal tunnel home 90 may be used in the operative procedure described herein in place of the carpal tunnel tome 50 shown in FIGS. 13 and 14.

Figure 18:
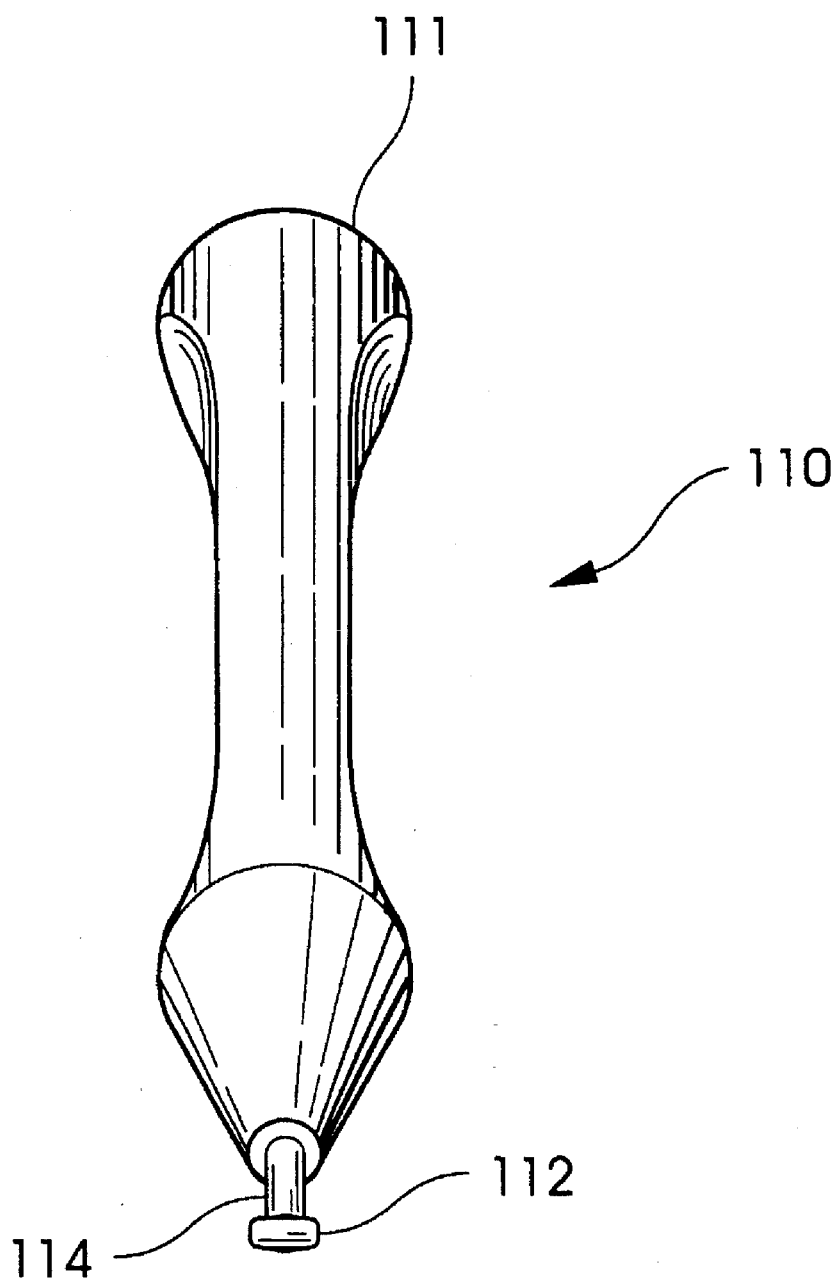

In FIGS. 16–18 there is shown an probe 110, which may be used in the operative procedure described herein below in place of the Freer elevator shown in FIG. 5. The probe 110 has a handle and stem similar to described in connection with the above embodiments shown in FIGS. 10–12, 15 and 19–21. As with those devices the handle 111 may be contoured to improve the ability of the user to grip the device. Further, as described above in connection with FIG. 10, the stem 114 may be angled, preferably to the same degree as the carpal tunnel tome to be used, near where the stem connects with the handle 111. However, in place of a cutting head, the probe 110 includes a single blunt, flat probe head 112 attached to the distal end of the stem 114. The width w' of the probe head 112 is designed to be the same width as the width of the lower protuberance of the cutting head of the carpal tunnel tome that will be used during the operative procedure. For example, if a carpal tunnel home of the type described in the above example given in connection with FIGS. 19–21 is used, then the width of the corresponding probe head 112 would be about 5 millimeters through the entire body portion of the probe head 112, with the exception of the very distal and very proximal ends of the probe head 112, which are rounded. Additionally, the probe head 112 is blunt, so as to not cause injury to the median nerve or flexor tendon as described therein.

The probe 110 is introduced into the incision before the carpal tunnel tome to ensure the unimpeded passage of the carpal tunnel tome. As such, the instrument may be passed down underneath the ligament prior to passing the actual cutting instrument so as to clear the path for the cutting instrument. The probe is used to gently disengage from the under-surface of the ligament any tissue that might be adherent thereto. As the width of the probe head is chosen to be the same as the greatest width of the lower protruberance of the carpal tunnel tome, no more tissue is disengaged from the ligament than is necessary to allow for passage of the cutting head.

Operative Procedure

The patient is brought to an outpatient operating room where approximately 10 cc of local anesthetic agent are infiltrated under the proximal palmar skin, across the wrist crease and into the sub fascial wrist compartment. Additional anesthetic material is also infiltrated directly into the carpal tunnel. Under tourniquet control, a 1–2 cm incision 41 is made between the thenar and hypothenar creases at the base of the distal edge of the thenar musculature on the palmar side 40 of the patient's hand as shown in FIG. 4. Sharp dissection is carried down to provide exposure, and a small Holzheimer self-retracting instrument 30 is usually repositioned several times as increasing depth of the incision is created by sharp and blunt dissection. A surgical sponge (not shown) may also be used to further clarify the level of dissection until the distal portion of the deep transverse carpal ligament 42 is clearly visualized through the incision, and all overhanging adipose tissue retracted.

Figure 5:
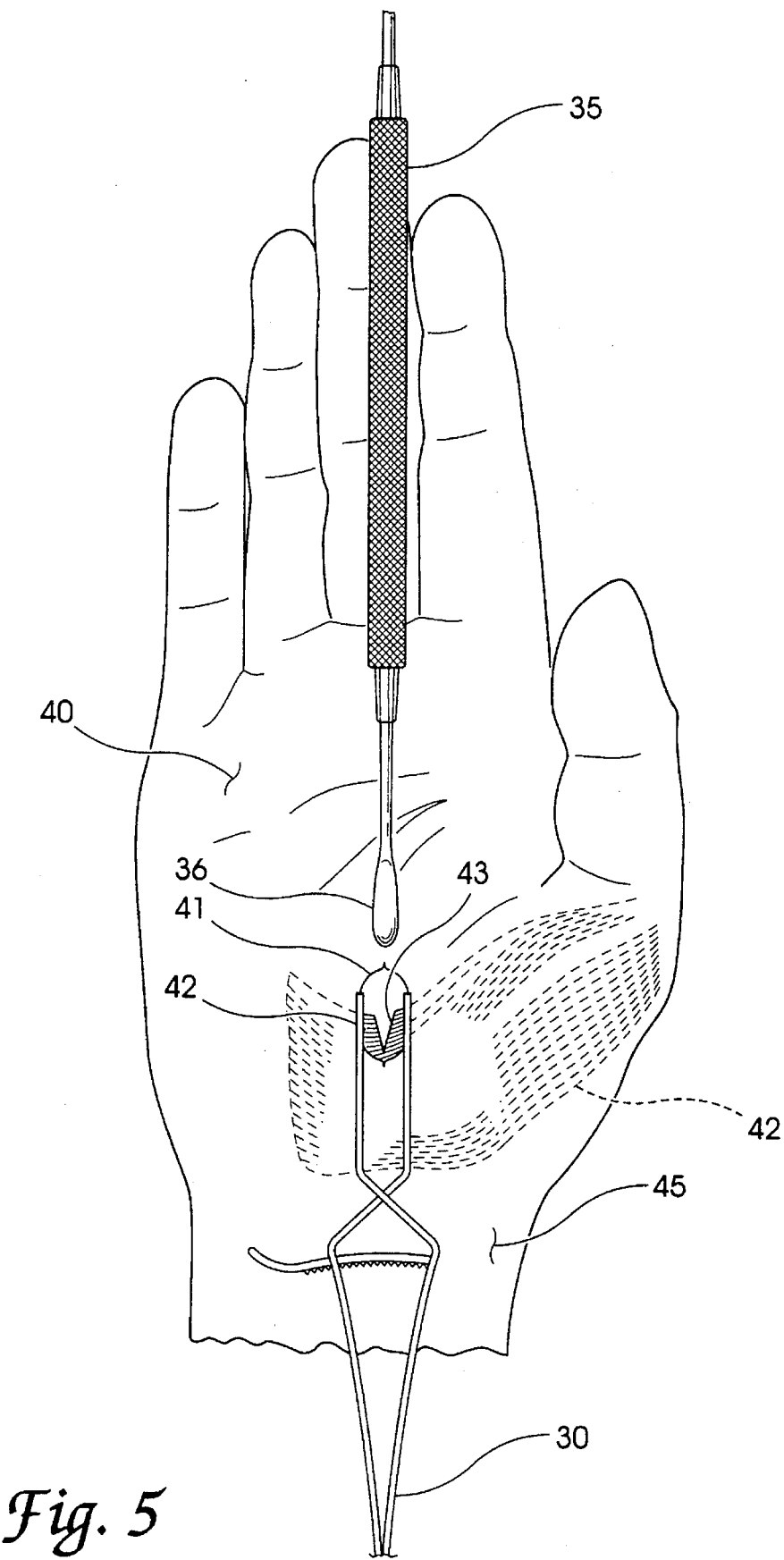
Figure 6:
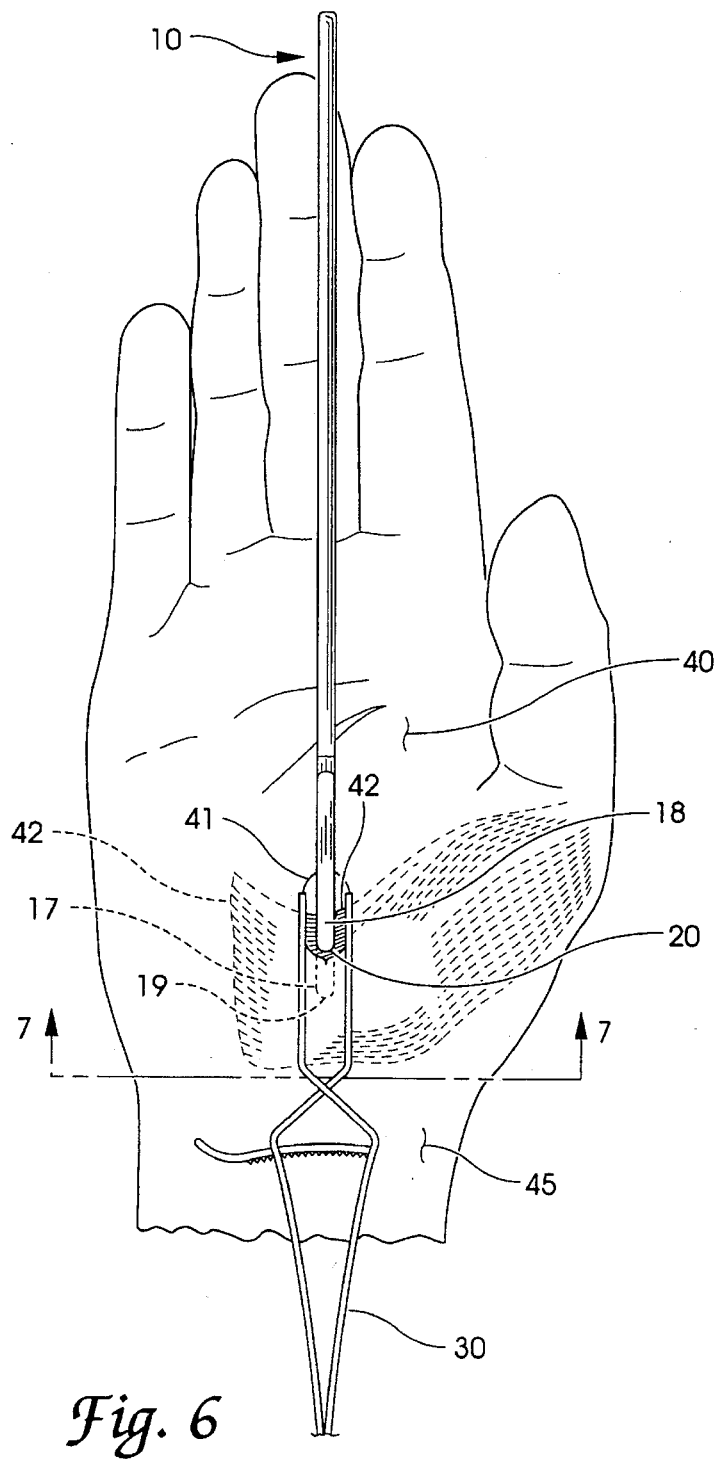
Figure 7:
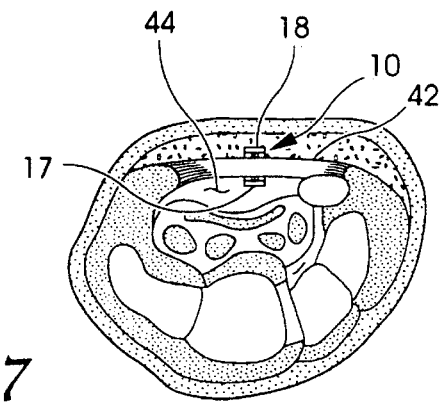
FIG. 7 is a cross-section through the patient's wrist at a midpoint in the surgery looking in the direction of arrows 7—7 of FIG. 6.
Figure 8:
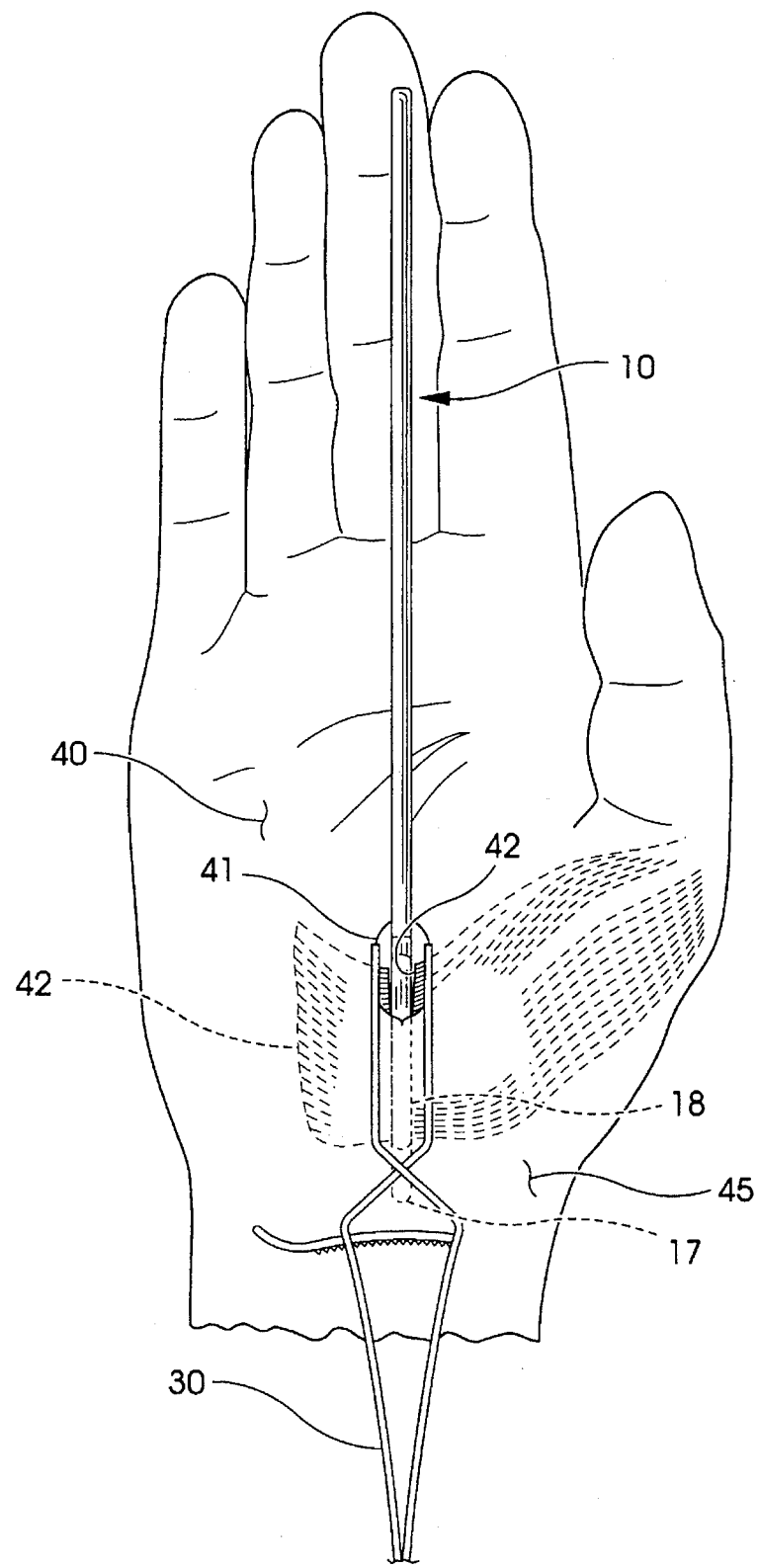

Referring now to FIG. 5, in the preferred method, the distal 1½ cm portion 43 of the ligament is then sharply divided, exposing the contents of the carpal vault. The curved end 36 of a Freer elevator 35 or the curved end 120 of the probe 110 is then placed beneath the partially divided ligament and gently passed proximately toward the patient's wrist 45 for 3–4 cm to separate the contents of the carpal tunnel from the ligament 42. Similarly, the Freer elevator or probe 110 may be passed on the palmar surface of ligament 42 to separate any fascial connections.

Figure 9:
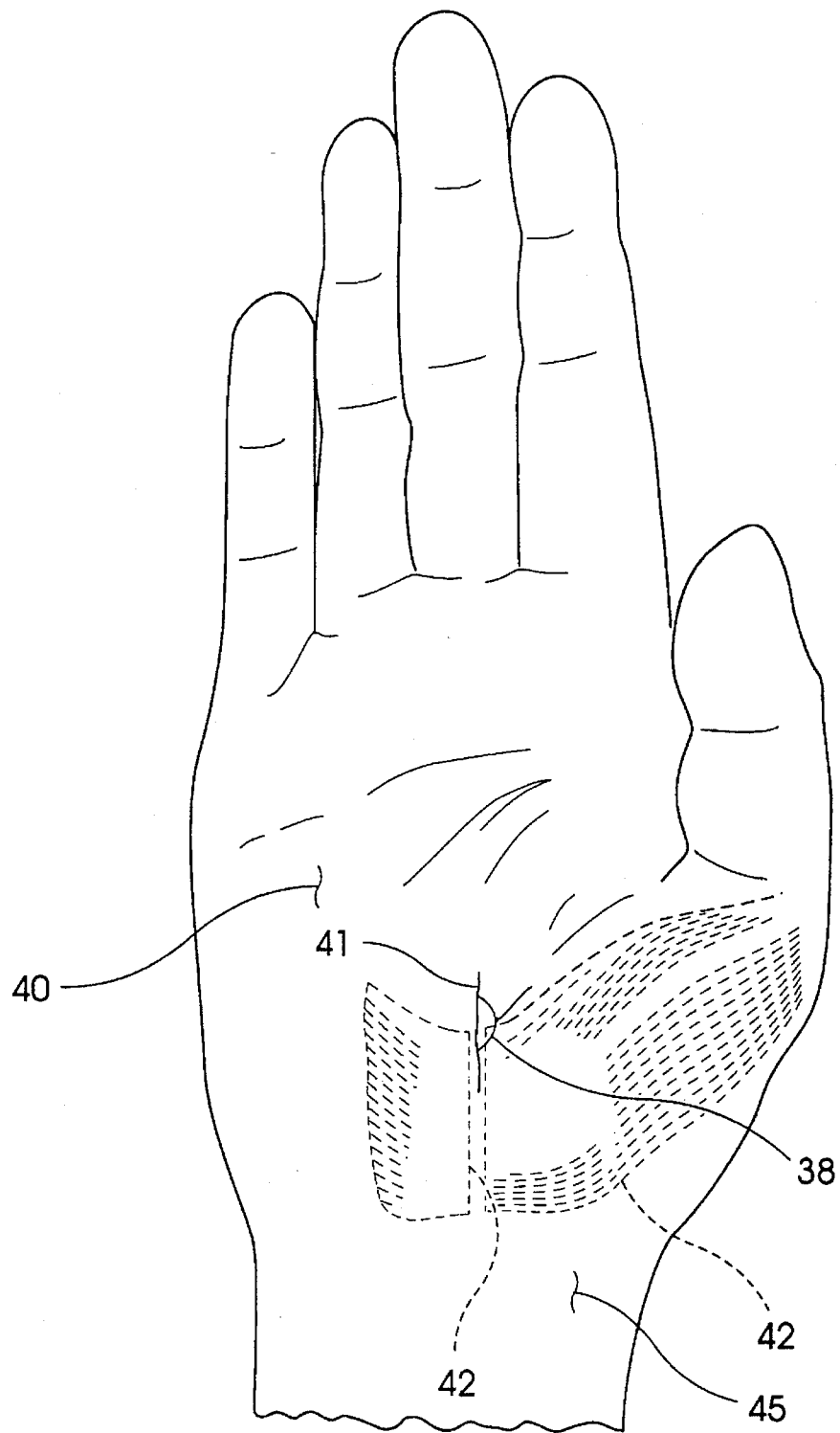

Next, as shown in FIGS. 6–8, and 13–14 the carpal tunnel home 10, 50, 70 or 90 is inserted into the wound with exposure being maintained by the Holzheimer self-restraining retractor 30. A small right-angle retractor (not shown) is preferably placed in the proximal aspect of the wound so that the leading protuberance 17 of tome 10, 57 of tome 50, 77 of tome 70, or 97 of tome 90 can be accurately placed beneath ligament 42 under direct vision. Once the surgeon is certain that protuberances 17 and 18 of tome 10, 57 and 58 of tome 50, 77 and 78 of tome 70, or 97 and 98 of tome 90 are straddling ligament 42, the carpal tunnel tome is passed proximately for 3–4 cm or until a definite lessening of resistance is felt. At this point, the tome 10, 50, 70 or 90 is withdrawn from the small wound allowing the surgeon to directly view the carpal tunnel 44 (FIGS. 7 and 14) and confirm the gapping between the radial and ulnar edges of the divided ligament; this allows the surgeon to confirm that the ligament 42 has been completely divided and the median nerve decompressed. Gently teasing the nerve to be sure that it is soft and nonadherent may then be carried out and a limited inspection of the carpal vault for any underlying lesions may also be done. After the wound has been irrigated, one or two sutures 38 are then used to close incision 41 as shown in FIG. 9. A small compressive dressing (not shown) is then applied from the distal forearm to the mid-palm, and the patient is encouraged to vigorously move his or her fingers.

By maintaining the position of the longer blunt protuberance 17 of instrument 10, 57 of instrument 50, 77 of instrument 70 or 97 of instrument 90 against the under-surface of ligament 42 as the instrument is advanced proximately, safety for the median nerve and palmar tendons is assured and the complete division of the ligament and its proximal fascial continuations is reliably achieved. Unlike the "blind" release afforded by endoscopic instruments, the relatively short mid-palmar incision of the present technique allows exposure and observation of the median nerve and the contents of the carpal vault, and allows for direct visual confirmation of the complete release of the ligament and expansion of the carpal tunnel.

After the surgery, the patient generally returns to the office in 10–14 days for suture removal. Early clinical results have indicated that the present technique results in markedly diminished palmar pain, with palmar pain discomfort and pillar pain being similar to that seen following endoscopic carpal tunnel release surgery. It is believed that the present technique results in less trauma to the patient and results in quicker post-operative recovery so that the patient is actually able to return to work at an earlier time than that possible with the techniques of the prior art. There is every reason to believe that the method of the present invention provides results which are entirely comparable with endoscopic carpal tunnel release surgery.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A carpal-tunnel tome comprising:

an elongated handle having a proximal end and a distal end;

a stem having a proximal end and a distal end, said proximal end of said stem in contact with said distal end of said elongated handle;

a cutting head having a proximal end and a distal end, said proximal end of said cutting head connected to said distal end of said stem, said cutting head including a blade comprising a first side, a second side and a cutting edge, said cutting edge extending between said sides, said cutting edge pointing distally away from said stem;

a first protuberance attached to said cutting head along said first side of said blade and extending distally beyond said cutting edge, said first protuberance including a first surface contiguous to said first side of said blade; and a second protuberance attached to said cutting head along said second side of said blade and extending distally beyond said cutting edge, said second protuberance including a second surface contiguous to said second side of said blade, said first protuberance extending distally away from said cutting edge a larger distance than said second protuberance;

wherein said first the surface is relatively flat and substantially parallel to said second surface.

2. The carpal tunnel tome of claim 1, wherein said stem has a body portion and an angled portion and wherein said angled portion is angled $\phi°$ from a plane running parallel to said body portion, and wherein $\phi°$ is not zero degrees.

3. The carpal tunnel tome of claim 2, wherein said first protuberance includes a tip portion distal from said cutting edge and wherein said distal tip is relatively blunt, at least a portion of said distal tip portion of said first protuberance having a greater thickness than a portion of said first protuberance proximal to said cutting head.

4. The carpal tunnel tome of claim 3, wherein at least a portion of the width of said distal tip portion of said first protruberance is greater than the width of said second protruberance.

5. The carpal tunnel tome of claim 4, wherein said second protuberance includes a distal tip, said distal tip being tapered.

6. The carpal tunnel tome of claim 2, wherein said angle $\phi°$ is 30°.

7. The carpal tunnel tome of claim 1 wherein said stem, said handle and at least a portion of said cutting head are integrally formed.

8. The carpal tunnel tome of claim 7 wherein a portion of said blade and said second protuberance may be detached from the remainder of said cutting head.

9. The carpal tunnel tome of claim 8 wherein said blade and said second protuberance are made from metal and said handle, said stem and said at least a portion of said cutting head are made from a plastic material.

10. The carpal tunnel tome of claim 9, wherein said stem has a body portion and an angled portion and wherein said angled portion is angled $\phi°$ from a plane running parallel to said body portion, wherein $\phi°$ is not zero degrees.

11. The carpal tunnel tome of claim 1 wherein said cutting edge is generally U-shaped.

12. The carpal tunnel tome of claim 1 wherein said width of said blade is about 3 millimeters.

13. The carpal tunnel tome of claim 12 wherein said protuberances are about 3 millimeters apart.

14. The carpal tunnel tome of claim 13 wherein said tip portion of said first protuberance includes a rounded end.

15. The carpal tunnel home of claim 14 wherein at least a portion of said first protuberance is wider than said second protruberance.

16. The carpal tunnel tome of claim 15 wherein said second protuberance is tapered.

17. The carpal tunnel tome of claim 16 wherein said first protuberance is about 2.75 millimeters thick at its distal tip and tapers to about 2 millimeters thick away from its distal tip.

18. The carpal tunnel tome of claim 17 wherein said handle is contoured to provide improved gripping of said handle.

19. The carpal tunnel tome of claim 17 wherein said handle and said stem have the same cross section and are a single piece.

20. A carpal tunnel tome comprising:

a stem having a proximal end and a distal end;

a cutting head having a proximal end and a distal end, said proximal end of said cutting head connected to said distal end of said stem, said cutting head including a blade comprising a first side, a second side and a cutting edge extending between said sides, said cutting edge pointing distally away from said stem;

a first protuberance attached to said cutting head along said first side of said blade and extending distally beyond said cutting edge; and a second protuberance attached to said cutting head along said second side of said blade and extending distally beyond said cutting edge;

wherein said stem has a body portion and an angled portion and wherein said angled portion is angled $\phi°$ from a plane running parallel to said body portion, wherein $\phi°$ is not zero degrees.

21. The carpal tunnel tome of claim 20 wherein said first protuberance additionally includes a first surface contiguous to said first side of said blade, and wherein said second protuberance includes a second surface contiguous to said second side of said blade, and wherein said first surface is relatively flat and substantially parallel to said second surface.

22. The carpal tunnel tome of claim 20 wherein said blade has a width; and said first protuberance extends distally beyond said cutting edge a distance greater than said width.

23. The carpal tunnel tome of claim 20 additionally including an elongated handle having a proximal end and a distal end, said proximal end of said stem in contact with said distal end of said elongated handle, said handle being contoured to improve a user's grip on said handle.

24. The carpal tunnel tome of claim 20, wherein at least a portion of the width of said first protruberance is greater than the width of said second protruberance.

25. A carpal tunnel tome comprising:

an elongated slender handle having a proximal end and a distal end;

a blade attached to said distal end and having a first side, a second side and a cutting edge extending between said sides, said cutting edge pointing distally away from said distal end;

a first unitary relatively blunt substantially straight protuberance attached to said distal end along said first side of said blade and extending distally beyond said cutting edge; and a second unitary relatively blunt substantially straight protuberance attached to said distal end along said second side of said blade and extending distally beyond said cutting edge;

wherein said blade is contacted on said first side only by said first unitary protuberance and wherein said blade is contacted on said second side only by said second unitary protuberance; and wherein said first protuberance extends distally away from said cutting edge a significantly larger distance than said second protuberance, 26. The carpal tunnel tome of claim 25 wherein said protuberances have a rounded end.

27. The carpal tunnel tome of claim 26 wherein said first protuberance is substantially parallel to said second protuberance.

28. The carpal tunnel tome of claim 27 wherein said cutting edge is concave.

29. The carpal tunnel tome of claim 25 wherein said blade has a width; and said first protuberance extends distally beyond said cutting edge a distance greater than said width.

30. The carpal tunnel tome of claim 29 wherein said width said blade is about 3 millimeters.

31. The carpal tunnel tome of claim 30 wherein said protuberances are substantially parallel and about 3 millimeters apart.

32. The carpal tunnel tome of claim 31 wherein said protuberances are substantially flat with a rounded end.

33. The carpal tunnel tome of claim 32 wherein said protuberances are about 1 millimeter thick.

34. A carpal tunnel tome comprising:
- a handle having an elongated slender distal end portion;
- a blade attached to said distal end portion and having a first side, a second side and a cutting edge extending between said sides, said cutting edge pointing distally away from said distal end portion;
- a first unitary relatively blunt substantially straight protuberance attached to said distal end portion along said first side of said blade and extending distally beyond said cutting edge; and
- a second unitary relatively blunt substantially straight protuberance attached to said distal end along said second side of said blade and extending distally beyond said cutting edge;
- wherein said blade is contacted on said first side only by said first unitary protuberance and on said second side only by said second unitary protuberance; and
- said distal end portion of said handle having dimensions in cross section which are no greater in height and width than the dimensions in cross section of the blade and protuberances.

* * * * *